United States Patent
Li et al.

(10) Patent No.: US 11,965,217 B2
(45) Date of Patent: Apr. 23, 2024

(54) **METHOD AND KIT FOR DETECTING *MYCOBACTERIUM TUBERCULOSIS***

(71) Applicant: Delta Electronics, Inc., Taoyuan (TW)

(72) Inventors: Yi-Chen Li, Taoyuan (TW);
Chih-Cheng Tsou, Taoyuan (TW);
Min-Hsien Wu, Taoyuan (TW);
Hsin-Yao Wang, Taoyuan (TW);
Chien-Ru Lin, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 215 days.

(21) Appl. No.: 17/328,762

(22) Filed: May 24, 2021

(65) Prior Publication Data

US 2022/0025441 A1    Jan. 27, 2022

Related U.S. Application Data

(60) Provisional application No. 63/054,417, filed on Jul. 21, 2020.

(51) Int. Cl.
*C12Q 1/68* (2018.01)
*C12Q 1/686* (2018.01)
*C12Q 1/689* (2018.01)

(52) U.S. Cl.
CPC .............. *C12Q 1/689* (2013.01); *C12Q 1/686* (2013.01)

(58) Field of Classification Search
None
See application file for complete search history.

(56) References Cited

U.S. PATENT DOCUMENTS

| | | | |
|---|---|---|---|
| 5,731,150 A | 3/1998 | Sandhu et al. | |
| 6,287,820 B1 * | 9/2001 | Umansky | C12Q 1/6879 536/23.1 |
| 7,329,493 B2 | 2/2008 | Chou et al. | |
| 10,301,686 B2 | 5/2019 | Kim | |
| 2002/0119478 A1 * | 8/2002 | Umansky | C12Q 1/6806 435/6.16 |
| 2003/0050470 A1 * | 3/2003 | An | C07H 21/00 435/6.14 |
| 2004/0023207 A1 * | 2/2004 | Polansky | A61K 48/005 435/456 |
| 2019/0264261 A1 * | 8/2019 | Tsou | C12Q 1/689 |
| 2021/0310047 A1 * | 10/2021 | Kuellmer | C12Q 1/686 |

FOREIGN PATENT DOCUMENTS

| | | | |
|---|---|---|---|
| CN | 103509790 B | 9/2015 | |
| TW | 201408779 A | 3/2014 | |
| WO | WO-2019023243 A1 * | 1/2019 | ........... C12Q 1/6844 |
| WO | WO-2020025222 A1 * | 2/2020 | ........... C12Q 1/686 |

OTHER PUBLICATIONS

Aryan et al., 2010. A novel and more sensitive loop-mediated isothermal amplification assay targeting IS6110 for detection of *Mycobacterium tuberculosis* complex. Microbiological research, 165(3), pp. 211-220. (Year: 2010).*
Bhawsar et al., 2017. TBSURE: An Improved Multiplex Real-Time PCR for TB Detection and Differentiation from Nontuberculous Mycobacterial Diseases in Adult Indian Population. Mycobact Dis, 7(232), pp. 2161-1068. (Year: 2017).*
Chaiprasert et al., 2006. One-tube multiplex PCR method for rapid identification of *Mycobacterium tuberculosis*. Southeast Asian journal of tropical medicine and public health, 37(3), p. 494-502. (Year: 2006).*
Comin et al., 2022. In-depth Analysis of IS6110 Genomic Variability in the *Mycobacterium tuberculosis* Complex. Frontiers in Microbiology, vol. 13, article 767912, pp. 1-11. (Year: 2022).*
Coros et al., 2008. IS 6110, a *Mycobacterium tuberculosis* complex-specific insertion sequence, is also present in the genome of *Mycobacterium smegmatis*, suggestive of lateral gene transfer among Mycobacterial species. Journal of bacteriology, 190(9), pp. 3408-3410. (Year: 2008).*
Cribb, P., Scapini, J.P. and Serra, E., 2002. One-tube nested polymerase chain reaction for detection of Chlamydia trachomatis. Memorias do Instituto Oswaldo Cruz, 97, pp. 897-900. (Year: 2002).*
Donoghue et al., 2011. Detection and characterization of *Mycobacterium tuberculosis* DNA in 18th century Hungarians with pulmonary and extra-pulmonary tuberculosis. Yearbook of Mummy Studies, c 2011 by Verlag Dr. Friedrich Pfeil, Munchen, Germany—ISBN 978-3-89937-137-6, vol. 1, pp. 51-56, (Year: 2011).*
Fletcher et al., 2003. Widespread occurrence of *Mycobacterium tuberculosis* DNA from 18th-19th century Hungarians. American Journal of Physical Anthropology: The Official Publication of the American Association of Physical Anthropologists, 120(2), pp. 144-152. (Year: 2003).*
Genbank Accession No. MZ574188—*Mycobacterium tuberculosis* strain TB1693 insertion sequence IS6110,partial sequence ( submitted Jul. 16, 2021, retrieved on Feb. 15, 2023 from http://www.ncbi.nlm.nih.gov/nuccore/MZ574188). (Year: 2021).*
Genbank Accession No. X17348—*Mycobacterium tuberculosis* IS6110 IS-like element (submitted Nov. 15, 1989, retrieved on Feb. 15, 2023 from http://www.ncbi.nlm.nih.gov/nuccore/X17348). (Year: 1989).*
Genbank Accession No. V00638—Lambda genome from map unit 74 backward to map unit 67 (submitted Jul. 23, 2016, retrieved on Feb. 15, 2023 from http://www.ncbi.nlm.nih.gov/nuccore/V00638). (Year: 2016).*
Genbank Accession No. NC_001416—Enterobacteria phage lambda, complete genome (submitted Aug. 1, 2000, retrieved on Feb. 16, 2023 from http://www.ncbi.nlm.nih.gov/nuccore/NC_001416). (Year: 2000).*

(Continued)

*Primary Examiner* — Samuel C Woolwine
*Assistant Examiner* — Olayinka A Oyeyemi
(74) *Attorney, Agent, or Firm* — KIRTON McCONKIE; Evan R. Witt (57) ABSTRACT

A method and a kit for detecting *Mycobacterium tuberculosis* are provided. The method includes a step of performing a nested qPCR assay to a specimen. The nested qPCR assay includes a first round of amplification using external primers and a second round of amplification using internal primers and a probe. The external primers have sequences of SEQ ID NOs. 1 and 2, and the internal primers and the probe have sequences of SEQ ID NOs. 3 to 5.

10 Claims, 3 Drawing Sheets

Specification includes a Sequence Listing.

(56) References Cited

OTHER PUBLICATIONS

Gengvinij et al., 2001. Detection of *Mycobacterium tuberculosis* from sputum specimens using one-tube nested PCR. Southeast Asian journal of tropical medicine and public health, 32(1), pp. 114-125. (Year: 2001).*

Gerriets et al., 2008. Implementation of a T4 extraction control for molecular assays of cerebrospinal fluid and stool specimens. The Journal of Molecular Diagnostics, 10(1), pp. 28-32. (Year: 2008).*

Leite et al., 2006. Rapid molecular diagnosis of tuberculosis and other *Mycobacteriosis* in smear-negative clinical specimens. Revista de Ciencias Farmaceuticas Basica e Aplicada, pp. 127-132. (Year: 2006).*

Leung et al., 2018. Diagnostic evaluation of an in-house developed single-tube, duplex, nested IS6110 real-time PCR assay for rapid pulmonary tuberculosis diagnosis. Tuberculosis, 112, pp. 120-125. (Year: 2018).*

Pham et al., 1998. Use of lambda phage DNA as a hybrid internal control in a PCR-enzyme immunoassay to detect Chlamydia pneumoniae. Journal of clinical microbiology, 36(7), pp. 1919-1922. (Year: 1998).*

SantaLucia Jr, John. Physical principles and visual-OMP software for optimal PCR design. PCR Primer Design. Humana Press, 2007: pp. 3-33. (Year: 2007).*

Sinha et al., (2016) Differentiation of *Mycobacterium tuberculosis* complex from non-tubercular *Mycobacteria* by nested multiplex PCR targeting IS6110, MTP40 and 32kD alpha antigen encoding gene fragments. BMC Infect. Dis., 16(1):123, pp. 1-10. (Year: 2016 ).*

Thacker et al., 2011. Improved specificity for detection of *Mycobacterium bovis* in fresh tissues using IS6110 real-time PCR. BMC Veterinary Research, 7(1), pp. 1-5. (Year: 2011).*

Wang et al., 2019. Development of a high sensitivity TaqMan-based PCR assay for the specific detection of *Mycobacterium tuberculosis* complex in both pulmonary and extrapulmonary specimens. Scientific Reports, 9(1), pp. 1-12. (Year: 2019).*

Yam et al., 2004. Direct detection of *Mycobacterium tuberculosis* in clinical specimens using single-tube biotinylated nested polymerase chain reaction-enzyme linked immunoassay (PCR-ELISA). Diagnostic microbiology and infectious disease, 48(4), pp. 271-275. (Year: 2004).*

Yuen et al., 1997. Comparison of two automated DNA amplification systems with a manual one-tube nested PCR assay for diagnosis of pulmonary tuberculosis. Journal of Clinical Microbiology, 35(6), pp. 1385-1389. (Year: 1997).*

Wang, H.Y., Development of a high sensitivity TaqMan-based PCR assay for the specific detection of *Mycobacterium tuberculosis* complex in both pulmonary and extrapulmonary specimens. Sci Rep, 2019. 9(1): p. 113.

World Health Organization, Global tuberculosis report 2020. 2020.

Caulfield, A.J. and N.L. Wengenack, Diagnosis of active tuberculosis disease: From microscopy to molecular techniques. J Clin Tuberc Other Mycobact Dis, 2016. 4: p. 33-43.

Chan, C.M., et al., Single-tube nested PCR in the diagnosis of tuberculosis. J Clin Pathol, 1996. 49(4): p. 290-4.

Prakash, U.B. and H.M. Reiman, Comparison of needle biopsy with cytologic analysis for the evaluation of pleural effusion: analysis of 414 cases. Mayo Clin Proc, 1985. 60(3): p. 158-64.

Nikam, C., et al., Rapid diagnosis of *Mycobacterium tuberculosis* with Truenat MTB: a near-care approach. PLoS One, 2013. 8(1): p. e51121.

Jason A. Jarzembowski, Michael B. Young. Nontuberculous *Mycobacterial* Infections, Arch Pathol Lab Med, vol. 132, Aug. 2008.

Babafemi EO, Cherian BP, Banting L, Mills GA, Ngianga K 2nd. Effectiveness of real-time polymerase chain reaction assay for the detection of *Mycobacterium tuberculosis* in pathological samples: a systematic review and meta-analysis. Syst Rev. 2017.25:215.

Costa et al., Enhanced Detection of Tuberculous Mycobacteria in Animal Tissues Using a Semi-Nested Probe-Based Real-Time PCR, PLOS One, Nov. 2013, 8(11), e81337.

* cited by examiner

| PCR program | IS6110 primer | DNA copy number | | | | | Primer Efficiency |
| --- | --- | --- | --- | --- | --- | --- | --- |
| | | $10^1$ | $10^2$ | $10^3$ | $10^4$ | $10^5$ | |
| | | Ct values | | | | | |
| NTB | + | 26.2 ±0.7 | 23.1 ±0.5 | 19.8 ±0.5 | 16.4 ±0.5 | 13.0 ±0.2 | 99.8% |
| CTB | - | 35.0 ±0.1 | 31.4 ±0.2 | 28.0 ±0.3 | 24.6 ±0.4 | 21.8 ±0.3 | 100.7% |

FIG. 3B

SEQUENCE LISTING

```
<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: Synthetically generated primer

<400> SEQUENCE: 1
gcagacctca cctatgtgtc gacctgggca                                      30

<210> SEQ ID NO 2
<211> LENGTH: 30
<212> TYPE: DNA
<213> ORGANISM: Artificial Sequence
<220> FEATURE:
<223> OTHER INFORMATION: Synthetically generated primer

<400> SEQUENCE: 2
tagaggcggc gatggttgaa ccagtcgacc                                      30

<210> SEQ ID NO 3
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 3
ctcgacctga aagacgttat cc                                              22

<210> SEQ ID NO 4
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 4
```

-continued

```
ctcggctagt gcattgtcat a                                              21

<210> SEQ ID NO 5
<211> LENGTH: 24
<212> TYPE: DNA
<213> ORGANISM: Artificial Sequence
<220> FEATURE:
<223> OTHER INFORMATION: Synthetically generated probe

<400> SEQUENCE: 5
agtacacatc gatccggttc agcg                                           24

<210> SEQ ID NO 6
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 6
tgcgatcagt aattcaaaac                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 7
gctcaatcaa ctcactaatg                                                20

<210> SEQ ID NO 8
<211> LENGTH: 24
<212> TYPE: DNA
<213> ORGANISM: Artificial Sequence
<220> FEATURE:
<223> OTHER INFORMATION: Synthetically generated probe

<400> SEQUENCE: 8
aaccacatac ttcctgcctt catt                                           24
```

METHOD AND KIT FOR DETECTING *MYCOBACTERIUM TUBERCULOSIS*

CROSS-REFERENCE TO RELATED APPLICATION

This application claims the benefit of U.S. Patent Provisional Application No. 63/054,417, filed on Jul. 21, 2020, and entitled as "TWO-STAGE NUCLEIC ACIDS AMPLIFICATION TESTING FOR SCREENING AND CONFIRMATION IN THE DIAGNOSIS OF *MYCOBACTERIUM TUBERCULOSIS* ACHIEVES A HIGHER SENSITIVITY AND SPECIFICITY", the entirety of which is hereby incorporated by reference.

FIELD OF THE INVENTION

The present invention relates to a method and a kit for detecting bacteria, and more particularly to a method and a kit for detecting *Mycobacterium tuberculosis*.

BACKGROUND OF THE INVENTION

Tuberculosis (TB) is an infectious disease caused by *Mycobacterium tuberculosis* (MTB) infection. Tuberculosis is one of the most important infectious diseases worldwide and kills 1.5 million people annually. To reduce the morbidity and mortality, and prevent TB transmission, accurate and rapid diagnosis at the early stage is particularly important.

The conventional TB diagnosis relies primarily on smear microscopic detection for acid fast bacilli (AFB), followed by TB culture on a selection medium. Although acid-fast staining (AFS) is a cost-efficient, rapid, and simple procedure, the overall detection sensitivity of TB is reported to be 71.4% in pulmonary specimens but it drops to 24% in extra-pulmonary specimens. For the latter, it is mainly due to the paucibacillary nature in the specimens and the fact that inhibitors are more common appearance in extra-pulmonary specimens than in pulmonary specimens (around 5-folds). In addition, AFS method could not distinguish between *M. tuberculosis* and non-tuberculosis mycobacteria (NTM). Currently, TB culture is regarded as the gold standard method for TB diagnosis. Compared with the AFS method, however, the major drawbacks of TB culture are time-consuming (culture time: 3-8 weeks) and costly. Even though the TB culture shows high detection specificity (around 100%), its sensitivity is still low (around 39 to 80%), mainly resulted from the slow-growing nature of bacteria.

To tackle the abovementioned issue, various nucleic acid amplification tests (NAATs) have been developed for the detection of TB over the past few decades. In general, the detection sensitivity and specificity of NAATs are 64-100% and 74-99.3%, respectively. However, these performances vary for 40-84% in paucibacillary specimens. Various NAATs have been proved to have positivity of 95-100% in AFS positive and culture positive specimens, while positivity ranges from 40 to 60% in AFS negative pulmonary specimens. In addition, some reports have indicated that there are several inhibitors in sputum that might affect nucleic acid amplification to cause false negative NAAT results. This phenomenon rarely occurred in AFS positive specimens. Moreover, several sporadic or systematic errors (e.g., the primer/probe having cross-reactivity to NTM or other species of bacteria, virus and fungus) can cause false positivity of PCR results.

Therefore, to overcome the drawbacks of the conventional technologies, there is a need of developing a novel NAAT method with high sensitivity and specificity and capable of detecting TB accurately, rapidly and cost-effectively.

SUMMARY OF THE INVENTION

An object of the present invention is to provide a method and a kit for detecting *Mycobacterium tuberculosis*, which has fairly high sensitivity and specificity, and can reduce false positive results.

Another object of the present invention is to provide a method and a kit for detecting *Mycobacterium tuberculosis*, which achieves higher sensitivity and specificity for clinical diagnosis, and saves time and expense of clinical diagnosis.

In accordance with an aspect of the present invention, a method for detecting *Mycobacterium tuberculosis* is provided. The method includes a step of performing a nested qPCR assay to a specimen, wherein the nested qPCR assay includes a first round of amplification using external primers and a second round of amplification using internal primers and a probe, the external primers have sequences of SEQ ID NOs. 1 and 2, and the internal primers and the probe have sequences of SEQ ID NOs. 3 to 5.

In an embodiment, an annealing temperature of the first round of amplification is higher than that of the second round of amplification.

In an embodiment, concentrations of the external primers are greater than those of the internal primers.

In an embodiment, the nested qPCR assay includes an internal control, which uses Lambda phage DNA as a template, and uses primers and a probe having sequences of SEQ ID NOs. 6 to 8.

In accordance with another aspect of the present invention, a method for detecting *Mycobacterium tuberculosis* is provided. The method includes steps of: performing a screening by qPCR to a specimen using primers and a probe having sequences of SEQ ID NOs. 3 to 5; and performing a nested qPCR assay to the specimen having a positive result in the screening, wherein the nested qPCR assay includes a first round of amplification using external primers and a second round of amplification using internal primers and a probe, the external primers have sequences of SEQ ID NOs. 1 and 2, and the internal primers and the probe have sequences of SEQ ID NOs. 3 to 5.

In an embodiment, an annealing temperature of the first round of amplification is higher than that of the second round of amplification.

In an embodiment, concentrations of the external primers are greater than those of the internal primers.

In an embodiment, the nested qPCR assay includes an internal control, which uses Lambda phage DNA as a template, and uses primers and a probe having sequences of SEQ ID NOs. 6 to 8.

In accordance with a further aspect of the present invention, a kit for detecting *Mycobacterium tuberculosis* is provided. The kit includes external primers, internal primers and a probe, wherein the external primers have sequences of SEQ ID NOs. 1 and 2, the internal primers have sequences of SEQ ID NOs. 3 and 4, and the probe has a sequence of SEQ ID NO. 5.

In an embodiment, the kit further includes primers and a probe having sequences of SEQ ID NOs. 6 to 8 used for an internal control.

In an embodiment, the kit further includes Lambda phage DNA as an internal control template.

The above contents of the present invention will become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed. The drawings of all the embodiments of the present invention are merely schematic and do not represent true dimensions and proportions.

The present invention provides a method and a kit for detecting *Mycobacterium tuberculosis* by one-tube nested quantitative PCR (nested qPCR) assay. The nested qPCR assay mainly involves the use of two primer sets and a two-step procedure, including a first round of amplification by an external primer set first, then a second round of amplification by an inner primer set later. Compared with the conventional qPCR (or real-time PCR), the nested qPCR performs PCR reactions twice in one single tube. In the first round of amplification, the PCR reaction is performed with the external primer set at a higher annealing temperature (e.g. 65° C.). Then, in the second round of amplification, the PCR reaction is performed with the inner primer set at a lower annealing temperature (e.g. 60° C.), wherein the amplicons produced in the first round of amplification are used as templates of the second round of amplification, and the products are simultaneously detected by fluorescent probes, so as to achieve effective amplification and higher sensitivity and specificity.

Figure 1:
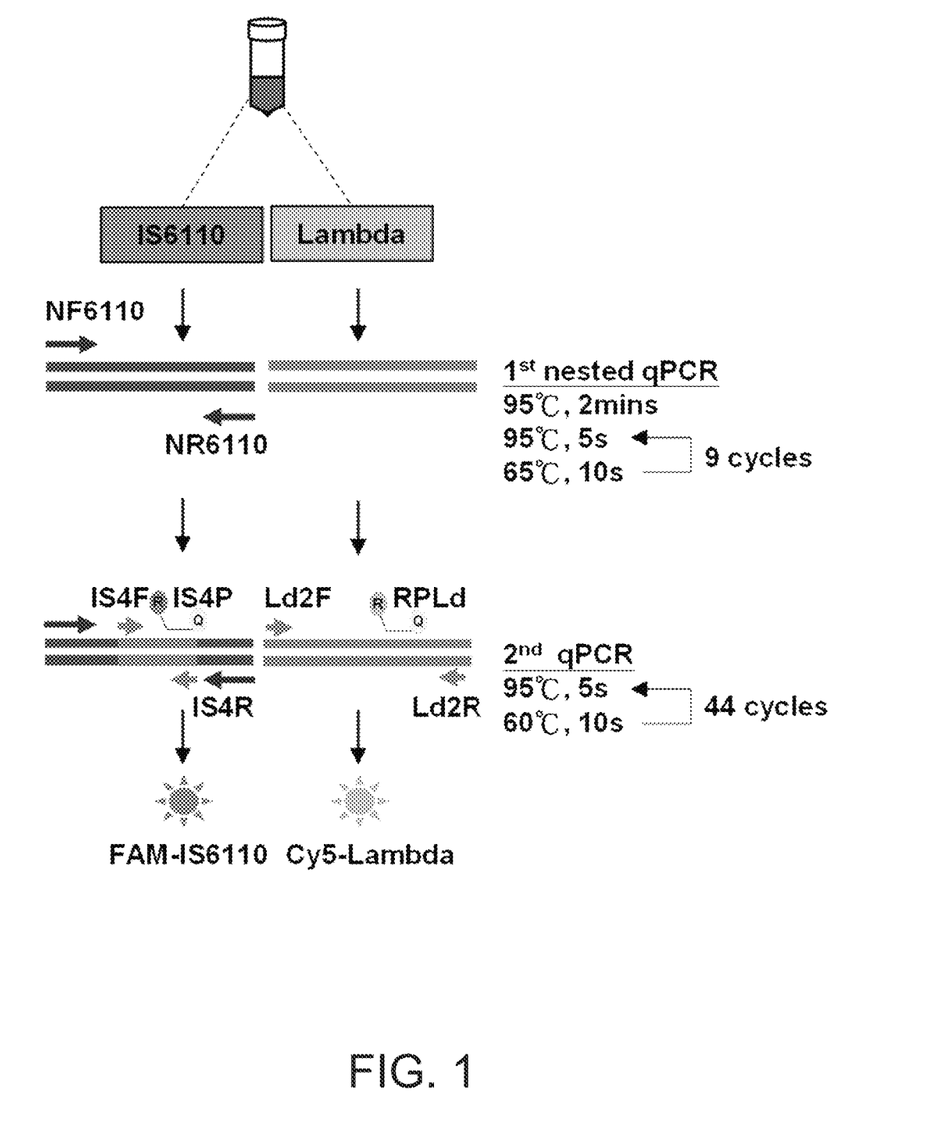
FIG. 1 shows a schematic view illustrating the nested qPCR of the present invention.

FIG. 1 shows a schematic view illustrating the nested qPCR of the present invention. First, a new external primer set is designed. The external primer set includes a forward primer NF6110 and a reverse primer NR6110, which are targeting the insertion sequence 6110 (IS6110) of *Mycobacterium tuberculosis* and capable of amplifying external fragments from IS6110 of *Mycobacterium tuberculosis*. An inner primer set were previously designed by the inventors of the present invention. The inner primer set includes a forward primer IS4F and a reverse primer IS4R, which are targeting the sequences between NF6110 and NR6110 of IS6110 and capable of amplifying shorter inner fragments from IS6110 of *Mycobacterium tuberculosis*. A fluorescent probe IS4P was also designed for the inner fragments to facilitate real-time detection. The sequences of the aforementioned NF6110, NR6110, IS4F, IS4R and IS4P are listed in the following Table 1.

TABLE 1

| Primer/Probe | Sequence | SEQ ID NO. |
| --- | --- | --- |
| NF6110 | 5'-GCAGACCTCACCTATGTGTCGACCTGGGCA-3' | 1 |
| NR6110 | 5'-TAGAGGCGGCGATGGTTGAACCAGTCGACC-3' | 2 |
| IS4F | 5'-CTCGACCTGAAAGACGTTATCC-3' | 3 |
| IS4R | 5'-CTCGGCTAGTGCATTGTCATA-3' | 4 |
| IS4P | 5'-AGTACACATCGATCCGGTTCAGCG-3' | 5 |

As shown in FIG. 1, in the first round of amplification, the PCR is performed to amplify a longer fragment with the first primer pair (NF6110 and NR6110) targeting IS6110 of *Mycobacterium tuberculosis*. In the second round of amplification, the longer amplicons produced by the first round of amplification are used as templates, and the PCR is performed to amplify a shorter fragment with the second primer pair (IS4F and IS4R) and the probe (IS4P). The probe IS4P is labeled with FAM (495-520 nm) to detect the shorter amplicons produced by the second round of amplification. Further, an internal control (Lambda phage DNA) is also co-amplified with a primer pair (Ld2F and Ld2R) and a probe (RPLd) in the second round of amplification, and the probe RPLd is labeled with Cy5 (646-662 nm) to detect the internal control amplicons produced by the second round of amplification. The sequences of Ld2F, Ld2R and RPLd are listed in the following Table 2.

TABLE 2

| Primer/Probe | Sequence | SEQ ID NO. |
| --- | --- | --- |
| Ld2F | 5'-TGCGATCAGTAATTCAAAAC-3' | 6 |
| Ld2R | 5'-GCTCAATCAACTCACTAATG-3' | 7 |
| RPLd | 5'-AACCACATACTTCCTGCCTTCATT-3' | 8 |

In an embodiment, the first round of amplification includes initial denaturation at 95° C. for 2 minutes, followed by 10 cycles of PCR amplification, and each cycle includes denaturation at 95° C. for 5 seconds and annealing/extension at 65° C. for 10 seconds. In an embodiment, the second round of amplification includes 45 cycles of PCR amplification, and each cycle includes denaturation at 95° C. for 5 seconds and annealing/extension at 60° C. for 10 seconds. The annealing temperature (65° C.) in the first round of amplification is higher than the annealing temperature (60° C.) in the second round of amplification, which facilitates increasing the sensitivity in the first round of amplification and increasing the specificity in the second round of amplification. Certainly, the amplification procedures in the first and the second rounds of amplification can be adjusted according to requirements, and are not limited to the aforementioned amplification procedures.

In addition, the reporter dyes labeled on the probes are not limited to the aforementioned FAM or CysS, and can also be ROX, HEX, TET, Texas Red, or other TaqMan fluorescent dyes, as long as the two selected fluorescent dyes are able to distinguish the amplicons from IS6110 and Lambda. Certainly, the template for internal control is not limited to Lambda phage DNA, and can be any template with known sequence.

In an embodiment, the primers for the first round of amplification and the primers/probes of the second round of amplification can be added to the reaction tube in different stages. For example, the external primers are firstly added to the reaction tube, and the internal primers and probe are later added to perform the second round of amplification after the first round of amplification is completed. In another embodiment, the primers for the first round of amplification and the primers/probe for the second round of amplification are added to the reaction tube together before the reaction, and the first round of amplification is prioritized due to different primer concentrations and different annealing temperatures. For example, the external primers, the internal primers, and the probe are added to the reaction tube simultaneously, wherein the concentrations of the external primers are greater than the concentrations of the internal primers, and the annealing temperature (e.g. 65° C.) of the first round of amplification is higher than the annealing temperature (e.g. 60° C.) of the second round of amplification. Consequently, the first round of amplification will proceed preferentially and produce a large number of external amplicons as templates for the second round of amplification. In some embodiments, the concentrations of the external primers are more than 2 times, 3 times, 4 times, or 5 times the concentrations of the inner primers, such as 2 to 6 times, but not limited thereto.

The following is an example to demonstrate the reaction conditions of the nested qPCR in the present invention. Each nested qPCR reaction mixture includes a master mix, which is purchased from TOYOBO and contains enzymes and buffer systems required for qPCR, 0.76 µM external primers (NF6110 and NR6110), 0.15 µM internal primers (IS4F and IS4R)), 0.15 µM IS6110 probe (IS4P), 0.3 µM internal control primers (Ld2F and Ld2R), 0.15 µM internal control probe (RPLd), 600 to 1000 copies of internal control template (Lambda phage DNA), and 4 µl of DNA extracted from the specimen or synthetic plasmid DNA containing IS6110 sequence, and the total volume is 13.2 µL. Subsequently, the first round of amplification is performed with the procedure including initial denaturation at 95° C. for 2 minutes, followed by 10 cycles of PCR amplification, and each cycle includes denaturation at 95° C. for 5 seconds and annealing/extension at 65° C. for 10 seconds. Then, the second round of amplification is performed with the procedure including 45 cycles of PCR amplification, and each cycle includes denaturation at 95° C. for 5 seconds and annealing/extension at 60° C. for 10 seconds. Certainly, the reaction mixture is not limited to the aforementioned enzymes and buffer systems, and the concentrations of the primers and the probes can also be adjusted according to requirements.

The efficacy of the nested qPCR for detecting *Mycobacterium tuberculosis* (hereinafter referred to as NTB) provided in the present invention is further tested and compared with the efficacy of the conventional qPCR for detecting *Mycobacterium tuberculosis* (hereinafter referred to as CTB) using IS4F, IS4R and IS4P. In other words, NTB uses NF6110 and NR6110 for the first round of amplification, and then uses IS4F, IS4R and IS4P for the second round of amplification, while CTB uses only IS4F, IS4R and IS4P for one round of amplification, which is equivalent to the second round of amplification in NTB.

Figure 2A:
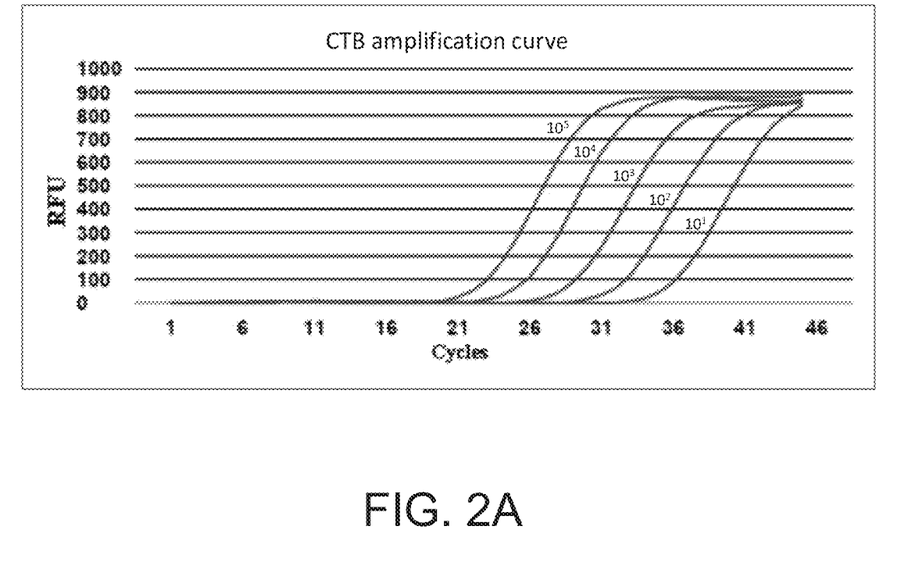
FIG. 2A shows the amplification curve of the conventional qPCR for detecting *Mycobacterium tuberculosis* (CTB assay)
Figure 2B:
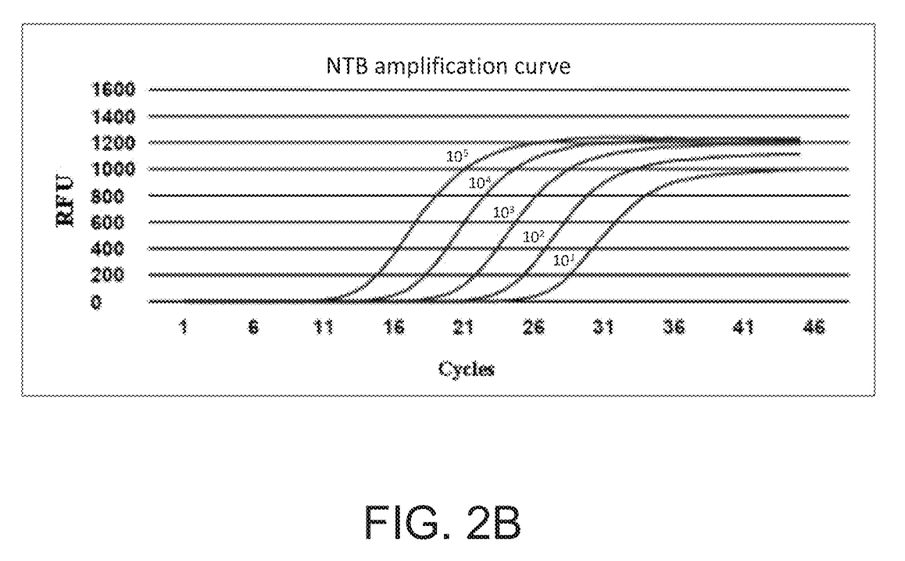
FIG. 2B shows the amplification curve of the nested qPCR of the present invention for detecting *Mycobacterium tuberculosis* (NTB assay)

FIGS. 2A and 2B show the amplification curves of CTB and NTB assays, respectively. The synthetic plasmid DNA containing IS6110 sequence was prepared in 10-fold serial dilutions to obtain $10^5$ to $10^1$ copies of plasmid DNA, and mixed with 1000 copies of Lambda phage DNA, and then analyzed by CTB and NTB. It is shown from FIGS. 2A and 2B that the increasing number of cycles was required to detect reducing DNA copies, and the fluorescence intensity (RFU) of NTB was higher than that of CTB.

Figure 3A:
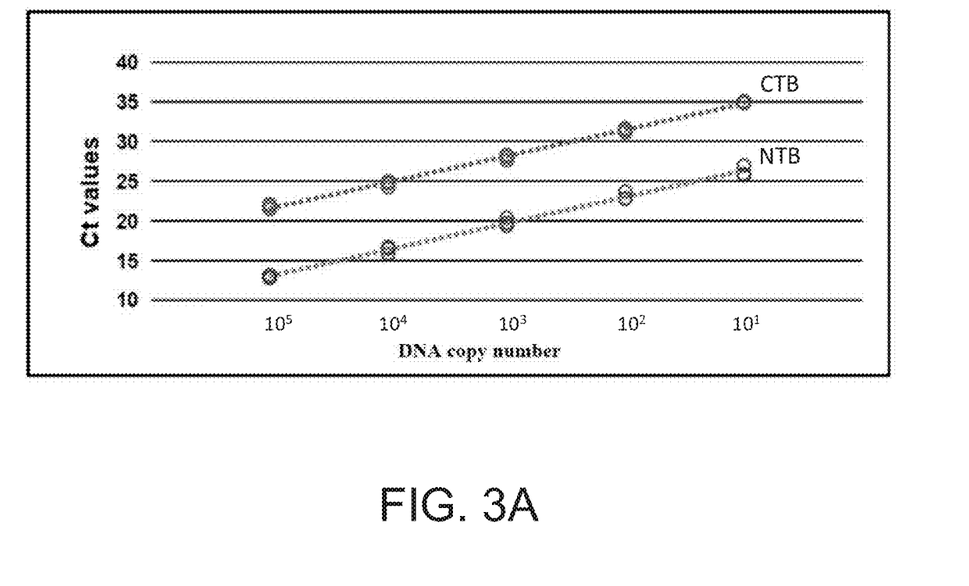
FIG. 3A shows the standard curves of CTB and NTB assays.
Figure 3B:
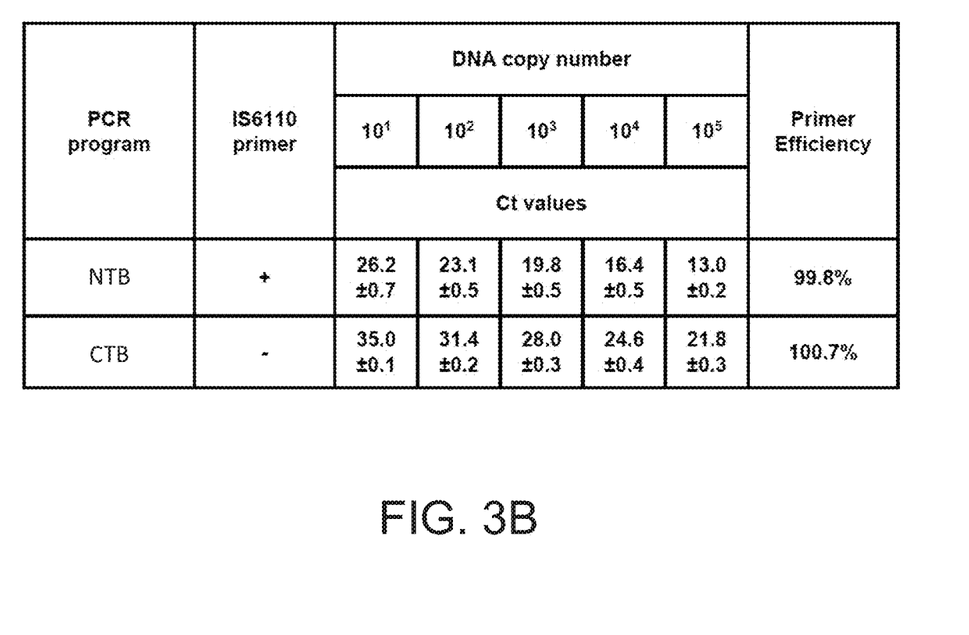
FIG. 3B shows the Ct values of CTB and NTB assays.

The amplification curves analyzed by CTB and NTB were further plotted into standard curves. FIG. 3A shows the standard curves of CTB and NTB assays, and FIG. 3B shows the Ct values of CTB and NTB assays. According to FIGS. 3A and 3B, the slopes of the standard curves of CTB and NTB were −3.31 and −3.32, respectively, and the primer amplification efficiency of CTB and NTB were 100.7% and 99.8%, respectively. The overall results showed that the correlation coefficient was approximate between CTB and NTB. In addition, compared with CTB (Ct values from 21.8 to 35.0), NTB had lower Ct values (from 13.0 to 26.2), which means that effective amplification in NTB assay may increase the sensitivity.

In order to determine the limit of detection (LOD) of NTB and CTB, 1 and 5 copies of IS6110-containing plasmid DNA were used to perform NTB and CTB assays, and all tests were performed in twenty replicates. The results are shown in Table 3 below. In the assays for 5 copies, both NTB and CTB had a positive rate of 100%, while in the assays for 1 copy, the positive rates of NTB and CTB were 85% (17/20) and 95% (19/20), respectively. Therefore, the limits of detection of NTB and CTB were estimated to be between 1 and 5 copies, both of which show a fairly high sensitivity.

TABLE 3

| DNA | NTB | | CTB | |
|---|---|---|---|---|
| COPY number | Average Ct values | Interpretation | Average Ct values | Interpretation |
| 5 | 27.5 ± 0.6 | Positive (20/20) | 36.5 ± 0.3 | Positive (20/20) |
| 1 | 30.2 ± 0.8 | Positive (17/20) | 39.2 ± 0.9 | Positive (19/20) |
| 0 | ND | Negative | ND | Negative |

Further, the specificities of NTB and CTB were also determined to ensure that the primers do not cross-react with other bacterial species. Therefore, the present invention also performed NTB and CTB assays on other non-tuberculosis mycobacteria (NTM), bacteria, and fungi. The tested NTMs included *M. abscessus, M. avium, M. chim aera-intracellulare* group, *M. cosmeticum, M. farcinogene senegalense* group, *M. fortuinum, M. gordonae, M. mageriitum, M. peregrinum, M. kansasii,* and *M. szulgai* in total 11 species. The tested bacteria included *A. baumannii*, B-Strepto. Gr. B, *E. coli, K. pneumoniae, P. aeruginosa,* and *S. epidermidis* in total 6 species. The tested fungi included *A. flavus, A. niger, C. albicans, C. guilliermondii, C. krusei, C. lusitaniae, C. tropicalis, S. apiospermum,* and *T. asahii* in total 9 species. The results showed that both NTB and CTB assays were negative for these NTMs, bacteria and fungi, which again showed that NTB and CTB were truly specific to *Mycobacterium tuberculosis*.

Moreover, clinical specimens were further used to test the efficacy of NTB and CTB in detecting *Mycobacterium tuberculosis*. The clinical specimens were 134 clinical specimens from Chang Gung Memorial Hospital, including 73 pulmonary specimens and 61 extra-pulmonary specimens. The pulmonary specimens included sputum (SP), bronchial washing (BW), and bronchoalveolar lavage fluid (BAL), while the extra-pulmonary specimens included tissue (TS), cerebrospinal fluid (CSF), pleural effusion (PL), pus, ascites (AS), fresh tissue (FTS), synovial fluid (SY), and deep tissue (DTS), etc. Using TB culture as the gold standard, these 134 clinical specimens included 79 culture positive specimens and 55 culture negative specimens. While distinguished by acid-fast staining (AFS) results, these 134 clinical specimens included 51 AFS positive specimens and 83 AFS negative specimens. The 134 clinical specimens were analyzed by NTB and CTB, and the results are shown in Table 4 below.

TABLE 4

|  | Culture positive | Culture negative |
|---|---|---|
| All specimens (n = 134) | | |
| CTB positive | 77 | 11 |
| CTB negative | 2 | 44 |
| NTB positive | 75 | 6 |
| NTB negative | 4 | 49 |
| Pulmonary specimens (n = 73) | | |
| CTB positive | 52 | 5 |
| CTB negative | 2 | 14 |
| NTB positive | 52 | 2 |
| NTB negative | 2 | 17 |
| Extra-pulmonary specimens (n = 61) | | |
| CTB positive | 25 | 6 |
| CTB negative | 0 | 30 |
| NTB positive | 23 | 4 |
| NTB negative | 2 | 32 |
| AFS positive specimens (n = 51) | | |
| CTB positive | 45 | 5 |
| CTB negative | 1 | 0 |
| NTB positive | 45 | 2 |
| NTB negative | 1 | 3 |
| AFS negative specimens (n = 83) | | |
| CTB positive | 32 | 6 |
| CTB negative | 1 | 44 |
| NTB positive | 30 | 4 |
| NTB negative | 3 | 46 |

It can be observed from Table 4 that among the 79 culture positive specimens, CTB positive and NTB positive were 77 (97.5%) and 75 (94.9%), respectively, while among the 55 culture negative specimens, CTB negative and NTB negative were 44 (80%) and 49 (89.1%), respectively. In other words, there were 11 false positives resulted by CTB and 6 false positives resulted by NTB, which means that NTB can rule out more false positive specimens (5 specimens). In pulmonary specimens and AFS positive specimens, the results of CTB and NTB for culture positive specimens were similar, and NTB further elicited the other three false positive results from 19 and 5 specimens, respectively. In extra-pulmonary specimens and AFS negative specimens, NTB elicited 2 false positive specimens from 36 and 50 culture negative specimens, respectively. Therefore, compared with CTB, NTB can reduce false positive results.

The diagnostic accuracies of NTB and CTB were further analyzed. With respect to TB culture as the gold standard, in all clinical specimens, the overall clinical sensitivity (true positive) and specificity (true negative) of CTB were 97.5% (77/79) and 80.0% (44/55), respectively, and the overall clinical sensitivity and specificity of NTB were 94.9% (75/59) and 89.1% (49/55), respectively. There was no difference between the sensitivities of CTB and NTB in pulmonary specimens and AFS positive specimens, but the specificity of NTB in pulmonary specimens is 89.5% (17/19), which is significantly better than 73.7% (14/19) of CTB, and the specificity in AFS positive specimens was increased from 0% (0/5) for CTB to 60% (3/5) for NTB. In extra-pulmonary specimens, the sensitivity and specificity of CTB were 100% (25/25) and 83.3% (30/36), respectively, while the sensitivity and specificity of NTB were 92.0% (23/25) and 88.9% (32/36), respectively. In AFS negative specimens, the sensitivity and specificity of CTB were 97.0% (32/33) and 88.0% (44/50), respectively, while the sensitivity and specificity of NTB were 90.9% (30/33) and 92.0% (46/50), respectively. The above results were summarized in Table 5 below. In overall, the sensitivity of CTB was slightly higher than that of NTB, and its performance was not compromised in extra-pulmonary specimens and AFS negative specimens. However, in all specimens from different groups, NTB was more specific than CTB. Therefore, using NTB in clinical detection can indeed effectively improve specificity and reduce false positive results, and even in extra-pulmonary specimens and AFS negative specimens, NTB still has a sensitivity of more than 90%.

TABLE 5

| Specimens | Assay | Sensitivity (%) | Specificity (%) |
|---|---|---|---|
| All specimens | CTB | 97.5 | 80.0 |
|  | NTB | 94.9 | 89.1 |
| Pulmonary specimens | CTB | 96.3 | 73.7 |
|  | NTB | 96.3 | 89.5 |
| Extra-pulmonary specimens | CTB | 100.0 | 83.3 |
|  | NTB | 92.0 | 88.9 |
| AFS positive specimens | CTB | 97.8 | 0 |
|  | NTB | 97.8 | 60.0 |
| AFS negative specimens | CTB | 97.0 | 88.0 |
|  | NTB | 90.9 | 92.0 |

From the above, the nested qPCR (NTB) of the present invention can indeed be used to detect *Mycobacterium tuberculosis*, and reveals fairly high sensitivity and specificity. Therefore, the present invention provides a method for detecting *Mycobacterium tuberculosis*, wherein the method includes performing the nested qPCR assays on specimens using the external primers NF6110 and NR6110 having sequences of SEQ ID NOs. 1 and 2 in the first round of amplification, and using the internal primers IS4F and IS4R and the probe IS4P having sequences of SEQ ID NOs. 3 to 5 in the second round of amplification. Also, the present invention provides a kit for detecting *Mycobacterium tuberculosis*. The kit includes the external primers NF6110 and NR6110 having sequences of SEQ ID NOs. 1 and 2, the internal primers IS4F and IS4R having sequences of SEQ ID NOs. 3 and 4, and the probe IS4P having sequences of SEQ ID NO. 5.

On the other hand, there are two testing platforms including screening test and confirmation test in clinical examinations. The screening test is usually cost effective and yields fast results, but there are likely to be more false test results due to lower sensitivity and specificity. In contrast, the confirmation test requires greater time and expense to perform than the screening test, but usually gives definite results. In the CTB assay, the overall sensitivity was 97.5%, but the specificity was only 80%. While in the NTB assay, the specificity was significantly increased to 89.1%. When comparing CTB and NTB, the CTB assay was cheaper and more rapid than the NTB assay, but the NTB assay gave a more precise result than the CTB assay. Under comprehensive consideration, due to the higher sensitivity of CTB, the present invention first performs CTB as screening test to screen suspected TB cases, and then performs NTB as confirmation test to confirm and rule out false positive results by means of the higher specificity of NTB. Such a two-stage nucleic acids amplification testing for screening and confirmation by CTB and NTB in the diagnosis of Mycobacterium tuberculosis can achieve higher sensitivity and specificity. Therefore, the present invention further provides a method for detecting Mycobacterium tuberculosis, which includes steps of: performing a screening by qPCR to a specimen using the primers IS4F and IS4R and the probe IS4P having sequences of SEQ ID NOs. 3 to 5; and performing a nested qPCR assay to the specimen having a positive result in the screening, wherein the nested qPCR assay comprises a first round of amplification using external primers and a second round of amplification using internal primers and a probe, the external primers have sequences of SEQ ID NOs. 1 and 2, and the internal primers and the probe have sequences of SEQ ID NOs. 3 to 5.

In conclusion, the present invention develops a new detection method and a detection kit for Mycobacterium tuberculosis through nested qPCR to amplify nucleic acids of Mycobacterium tuberculosis in the specimens. Firstly, the first round of amplification is carried out by using external primers NF6110 and NR6110. Then the second round of amplification is carried out by using the internal primers IS4F and IS4R, and the fluorescent probe IS4P is used for simultaneous detection. The nested qPCR provided in the present invention has fairly high sensitivity and specificity, which can reduce false positive results, and it still has a sensitivity of more than 90% even in extra-pulmonary specimens and AFS negative specimens. In addition, considering the time and expense of clinical diagnosis, the present invention further provides a two-stage testing, which first performs the screening by qPCR to specimens using the primers IS4F and IS4R and the probe IS4P, and then performs the confirmation by the nested qPCR assay to the specimen having a positive result in the screening. Accordingly, higher sensitivity and specificity for the clinical diagnosis of Mycobacterium tuberculosis can be achieved.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method for detecting *Mycobacterium tuberculosis*, comprising a step of performing a nested qPCR assay to a specimen, wherein the nested qPCR assay comprises a first round of amplification using external primers and a second round of amplification using internal primers and a probe, the external primers consist of sequences of SEQ ID NOs. 1 and 2, and the internal primers and the probe consist of sequences of SEQ ID NOs. 3 to 5.

2. The method for detecting *Mycobacterium tuberculosis* according to claim 1, wherein an annealing temperature of the first round of amplification is higher than that of the second round of amplification.

3. The method for detecting *Mycobacterium tuberculosis* according to claim 1, wherein concentrations of the external primers are greater than those of the internal primers.

4. The method for detecting *Mycobacterium tuberculosis* according to claim 1, wherein the nested qPCR assay comprises an internal control, which uses Lambda phage DNA as a template.

5. The method for detecting *Mycobacterium tuberculosis* according to claim 4, wherein primers and a probe consisting of sequences of SEQ ID NOs. 6 to 8 are used for the internal control.

6. A method for detecting *Mycobacterium tuberculosis*, comprising steps of:
   performing a screening by qPCR to a specimen using primers and a probe consisting of sequences of SEQ ID NOs. 3 to 5; and
   performing a nested qPCR assay to the specimen having a positive result in the screening, wherein the nested qPCR assay comprises a first round of amplification using external primers and a second round of amplification using internal primers and a probe, the external primers consist of sequences of SEQ ID NOs. 1 and 2, and the internal primers and the probe consist of sequences of SEQ ID NOs. 3 to 5.

7. The method for detecting *Mycobacterium tuberculosis* according to claim 6, wherein an annealing temperature of the first round of amplification is higher than that of the second round of amplification.

8. The method for detecting *Mycobacterium tuberculosis* according to claim 6, wherein concentrations of the external primers are greater than those of the internal primers.

9. The method for detecting *Mycobacterium tuberculosis* according to claim 6, wherein the nested qPCR assay comprises an internal control, which uses Lambda phage DNA as a template.

10. The method for detecting *Mycobacterium tuberculosis* according to claim 9, wherein primers and a probe consisting of sequences of SEQ ID NOs. 6 to 8 are used for the internal control.

\* \* \* \* \*